United States Patent
Fried

[11] 4,054,594
[45] Oct. 18, 1977

[54] SEPARATION OF DIASTEREOMERS

[75] Inventor: Joseph Fried, Chicago, Ill.

[73] Assignee: University of Chicago, Chicago, Ill.

[21] Appl. No.: 626,724

[22] Filed: Oct. 29, 1975

Related U.S. Application Data

[63] Continuation-in-part of Ser. No. 400,297, Sept. 24, 1973, abandoned, which is a continuation-in-part of Ser. No. 361,664, May 18, 1973, abandoned, which is a continuation-in-part of Ser. No. 53,663, July 9, 1970, abandoned.

[51] Int. Cl.$^2$ ............................................. C07C 125/06
[52] U.S. Cl. .................................. 560/32; 260/617 R
[58] Field of Search ...................................... 260/471 C

[56] References Cited
PUBLICATIONS

Eliel, *Stereochemistry of Carbon Compounds*, pp. 49–50, (1962).
Brutcher et al., J.A.C.S., 78, pp. 5695–5696 (1956).

*Primary Examiner*—Jane S. Myers

[57] ABSTRACT

A method of directly separating into its individual diastereomers, diastereomeric mixtures containing optically active compounds of the formulae

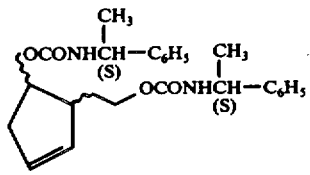

AND

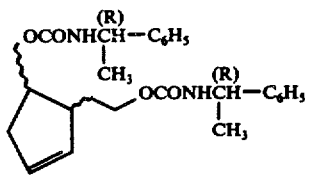

which comprises first crystallizing the said mixture from an aromatic hydrocarbon solvent to recover one diastereomer, and then recrystallizing the residue from a ketone to recover the remaining diastereomer.

5 Claims, No Drawings

SEPARATION OF DIASTEREOMERS

This application is a continuation in part application of my prior filed copending application Ser. No. 400,297, filed Sept. 24, 1973, now abandoned which is a continuation-in-part of Ser. No. 361,664, 5/18/73, now abandoned, which is continuation-in-part of Ser. No. 53,663, 7/9/70, now abandoned.

The invention described herein was made in the course of work done under a grant or award from the United States Department of Health, Education and Welfare.

This invention relates to and has as its objective a novel method of obtaining certain compounds having utility as intermediates in the production of various optically and pharmacologically active compounds. As disclosed in my prior filed copending application, Ser. No. 400,297, filed Sept. 24, 1973, an important intermediate for the production of the pharmacologically active final products of that invention is a compound of the formula

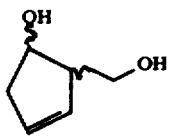

which is obtained as a racemic mixture of its optically active enantiomers. In order to be further employable in the production of the desired final products of my prior filed application Ser. No. 400,297 it is necessary to resolve this racemic mixture into its individual diol enantiometers of the formulae

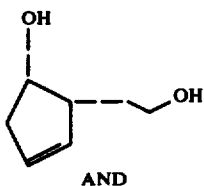

AND

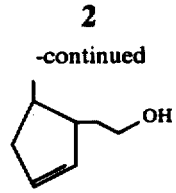

Heretofore, the resolution procedure employed involved a number of different and sophisticated chemical reactions which is not desirable due to poor yields, both quantitative and qualitative.

[Whenever in the formulae set forth in this specification and the claims attached hereto, a curved line (⌇) is employed in the linkage of atoms, it is intended to denote that the connected atom may be either in the α- or β-position, i.e. either above or below the plane of the paper, as is determined in each of the respective compounds involved.]

I have now discovered a novel method whereby a racemic mixture of optically active enantiomers having the formula

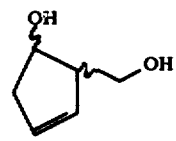

may be conveniently and easily resolved into their individual enantiomers of the formulae

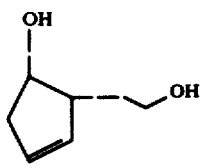

AND

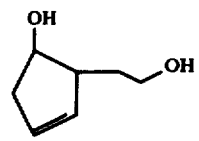

The method of my invention entails a procedure which can be represented by the following equations

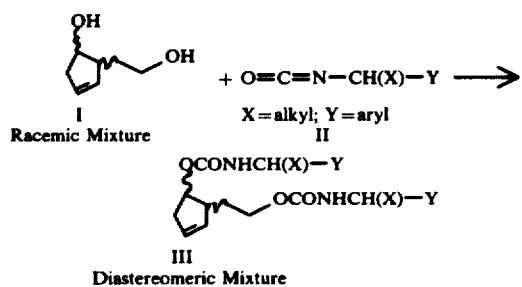

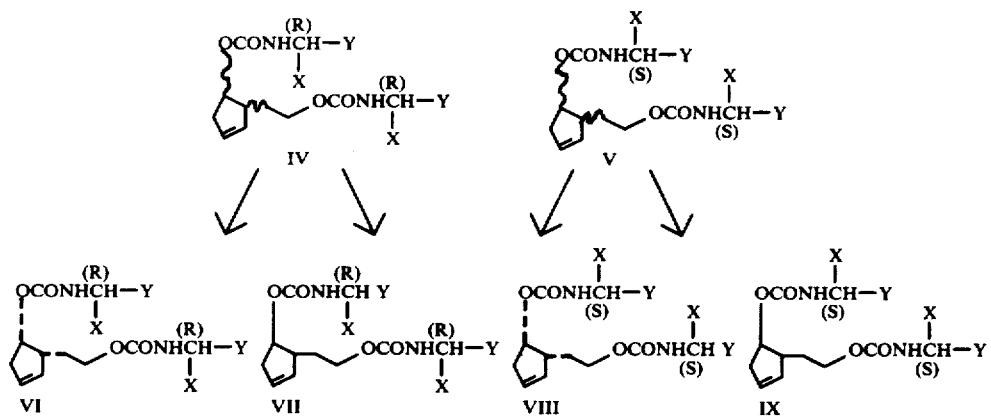

In the first step of the process of the instant invention the racemic diol (Compound I), which is obtained in accordance with the procedure set forth in my prior filed application Ser. No. 400,297, is treated with an optically active aralkyl isocyanate (Compounds II) for example, an aryl-lower alkyl isocyanate, such as α-phenethyl isocyanate, for example, (+)-(R)-α-phenethyl isocyanate or (−)-(S)-α-phenethyl isocyanate, to yield a mixture of the diastereomeric biscarbamates (Compounds III). The diastereomeric mixture thus obtained may then be separated to directly obtain and isolate the individual optically active diastereomers thereof. The diastereomeric mixture is first subjected to a crystallization treatment with an aromatic hydrocarbon solvent, for example benzene, toluene, xylene and the like, as the crystallization solvent. This aromatic hydrocarbon, e.g. benzene, crystallization procedure causes one diastereomeric compound to crystallize in pure form allowing removal thereof from the mixture. The residue of the diastereomeric mixture is then subjected to a crystallization treatment with a ketone solvent of crystallization, for example acetone, which results in the crystallization of the remaining diastereomeric compound therefrom in pure form. The resultant crystallized diastereomeric compounds thus isolated may then be further treated in accordance with the teachings of my prior filed application Serial No. 400,297, to yield the desired final products as set forth therein.

The invention may be illustrated by the following examples:

EXAMPLE 1

Preparation of (±)-cis-2-(2′-Hydroxyethyl)-cyclopent-3-enol

A solution of (+)-cis-2-(2′-Carboxymethylene)-cyclopent-3-enol) lactone in 50 ml of tetrahydrofuran was added with stirring over 15 min at 0° to a suspension of 1.74 g of lithium aluminum hydride in 100 ml of tetrahydrofuran. The mixture was stirred for an additional 45 min. at 0°, whereupon saturated aqueous potassium sodium tartrate was added dropwise until no further hydrogen was evolved. Excess anhydrous sodium sulfate was added, the mixture was filtered and the filter thoroughly washed with tetrahydrofuran. The solvent was evaporated at 30° to give a viscous pale yellow liquid which was distilled to give 3.5 g of the racemic diol olefin bp $_{1.6\,mm}$ 108°. (90% yield).

EXAMPLE 2

Resolution of the Cyclopentenediol Racemic Mixture a. Preparation of the (−)-Bis-(R)-N-(α-phenethyl)-carbamates of the racemic cyclopentenediol A solution of 29.94 g (2.34 mmoles) of the (±)-racemic cyclopentenediol and 79.2 g (539 mmoles) of (+)-(R)-α-phenethylisocyanate in 1 liter of freshly distilled sodium-dried toluene was refluxed under nitrogen for 36 hrs. On cooling to room temperature the biscarbamate (Compound VI) crystallized, which after washing with toluene furnished 33.3 g, mp 146°–148°. After one crystallization from benzene 29.2 g of pure biscarbamate (Compound VI) was obtained. Mp 150°–152° $\alpha_D^{49.5°}$ −61.6° (c, 0.95 in benzene).

Anal. Calcd for $C_{25}H_{30}O_4N_2$: C, 71.06; H, 7.16; N, 6.63 Found: C, 70.96; H, 7.00; N, 6.62.

The mother liquors remaining after removal of Compound VI were evaporated to dryness and the solid residue recrystallized from acetone to recover the diastereomeric biscarbamate (Compound VII). A total of 27.82 g was obtained, mp 131°–131.5° $\alpha_D^{20°}$ −53.3° (c, 1.07 in $CHCl_3$).

b. Preparation of (−)-cis-2-(2′-Hydroxyethyl)-cyclopent-3-enol

A solution of 2.2 g of the (−)-biscarbamate (Compound VI) in 25 ml of tetrahydrofuran was added at reflux to a suspension of 540 mg of lithium aluminum hydride in 75 ml of tetrahydrofuran and the mixture was stirred and refluxed for 2 hrs. It was then cooled and saturated aqueous potassium sodium tartrate was added dropwise until no further hydrogen was evolved. Excess anhydrous sodium sulfate was added, the suspension was filtered and the filter thoroughly rinsed with tetrahydrofuran. The solvent was evaporated in vacuo and the residue taken up in 20 ml of methanol. The resulting solution was passed through a column containing 10 g (2.5 equiv) of 50–100 mesh Dowex 50W-X8 previously washed with .1 N hydrochloric acid, distilled water and methanol and the column was rinsed with 20 ml of methanol. Evaporation of the solvent at 30° afforded 408 mg of a yellow oil which upon distillation afforded 408 mg of pure (−)-cyclopentenediol $\alpha_D^{25°}$ −60.5° (C, 1.03 in CHCl$_3$), −68° (c, 1.23 in CH$_3$OH).

c. Preparation of (+)-cis-2-(2'-Hydroxyethyl)-cyclopent-3-enol

Using the procedure of Example 2, section b above, but substituting an equivalent amount of the biscarbamate (Compound VII) for the diastereomer (Compound VI) there was obtained the (+)-cyclopentenediol $\alpha_D^{23°}$ +61.0° (c, 1.04 in CHCl$_3$).

EXAMPLE 3

Alternate Resolution of the Cyclopentenediol a. Preparation of the (+)-Bis-(S)-N-( -phenethyl)-carbamates of the Dihydroxypentenediols Following the procedure described in Example 2, section a, but substituting an equivalent amount of (−)-(S)-α-phenethylisocyanate for the (+)-(R)-α-phenethyisocyanate there was obtained by crystallization from benzene the pure biscarbamate (Compound IX) mp 150°–152° $\alpha_D^{50°}$ +60.2° (c, 0.98 in benzene). Evaporation of the mother liquors to dryness followed by recrystallization of the residue from acetone gave the pure biscarbamate (Compound VIII) mp 129°–131.5° $\alpha_D^{20°}$ +52.8° (c, 0.95 in CHCl$_3$).

b. Preparation of (−)-cis-2-(2'-Hydroxyethyl)-cyclopent-3-enol

Following the procedure described in Example 2 section (b) but substituting an equivalent amount of the (+)-biscarbamate (Compound VIII) for the (−)-biscarbamate (Compound VI) in the lithium aluminum hydride reduction there was obtained the pure (−)-cyclopentenediol $\alpha_D^{21.5°}$ −60.5° (c, 1.03 in CHCl$_3$); −68.1° (c, 1.23 in CH$_3$OH).

c. Preparation of (+)-cis-2-(2'-Hydroxyethyl)-cyclopent-3-enol

Following the procedure of Example 2 section (c) but substituting an equivalent amount of the biscarbamate (Compound IX) for its diastereomer (Compound VI) there was obtained the (+)-cyclopentenediol $\alpha_D^{23°}$ +61.0° (c, 1.04 in CHCl$_3$).

EXAMPLE 4

Preparation of (+)-all cis-2-(2'-Hydroxyethyl)-3,4-oxidocyclopent-anol

A solution of 2.4 g of 85% m-chloroperbenzoic acid in 30 ml of chloroform was added at 0° to a solution of 1.2 g of the (−)-cyclopentenediol in 20 ml of chloroform and the mixture was stirred at 0 for 3 hrs. Methanol was added to the resulting white suspension and the mixture was partially evaporated at room temperature. This was repeated twice and methanol was added to make up to 100 ml. This solution was passed through a short column containing 17.7 g (2.5 equiv) of 100–200 mesh Dowex 1-X8 previously washed with 300 ml of 0.5 N sodium hydroxide, distilled water and 300 ml of methanol and the column was rinsed with 150 ml of methanol. Evaporation of the solvent at 30° afforded a yellow oil which was distilled to give 1.435 g of pure (+)-epoxydiol as a viscous colorless liquid. Bp $_{.14mm\ Torr}$ 60° (99.6% yield). $\alpha_D^{25°}$ +2.7° (c, 2.36 in CHCl$_3$); −2.9° (c, 1.65 in CH$_3$OH).

Anal. Calcd for C$_7$H$_{12}$O$_3$. C, 58.31; H, 8.39. Found C, 58.33; H, 8.51.

EXAMPLE 5

Preparation of (−)-all cis-2-(2'-hydroxyethyl)-3,4-oxidocyclopentanol

Following the procedure of Example 4 but substituting an equivalent amount of the (+)-cyclopentenediol of Example 3 for its levorotatory antipode there was obtained the enantiomeric (−)-epoxydiol $\alpha_D^{24°}$ −2.6° (c, 0.99 in CHCl$_3$), +3.9° (c, 1.44 in CH$_3$OH).

The invention may be otherwise embodied within the scope of the appended claims.

What is claimed is:

1. A method of directly separating into its individual diastereomers, a diastereomeric mixture comprised of compounds of the formula

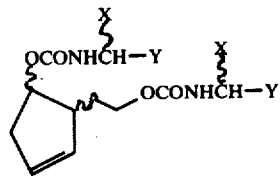

wherein X is methyl and Y is phenyl; which comprises subjecting said diastereomeric mixture to crystallization employing a aromatic hydrocarbon selected from the group consisting of benzene, toluene and xylene as crystallization solvent to obtain one diastereomer from said diastereomeric mixture and then subjecting the remainder of said diastereomeric mixture to crystallization with an acetone crystallization solvent to obtain the remaining diastereomer from said diastereomeric mixture.

2. The method of claim 1 wherein the aromatic hydrocarbon is benzene.

3. The method of claim 1 wherein the diastereomeric mixture may be comprised of optically active compounds of the formula

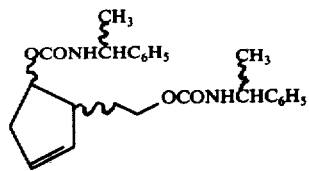

and the separated diastereomers are compounds of the formula

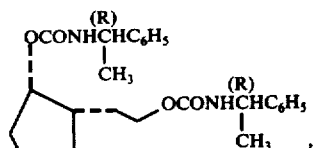

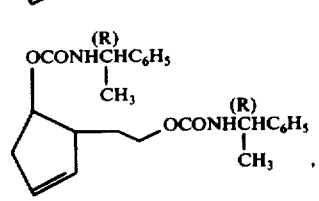

-continued
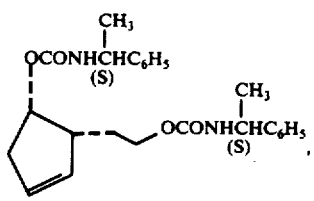
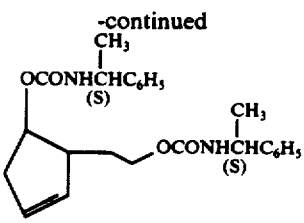
4. The method of claim 1, wherein the aromatic hydrocarbon is xylene.
5. The method of claim 1 wherein the aromatic hydrocarbon is toluene.